(12) United States Patent
Tanzer et al.

(10) Patent No.: US 6,570,056 B1
(45) Date of Patent: May 27, 2003

(54) ABSORBENT ARTICLE HAVING ZONED DIRECTIONAL STRETCHING

(75) Inventors: Richard Warren Tanzer, Neenah, WI (US); Thomas Walter Odorzynski, Green Bay, WI (US); Michael Tod Morman, Alpharetta, GA (US); Georgia Lynn Zehner, Larsen, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/384,597

(22) Filed: Aug. 27, 1999

(51) Int. Cl.[7] ................................................ A61F 13/15
(52) U.S. Cl. .............. 604/368; 604/385.16; 604/385.22
(58) Field of Search ................................. 604/367, 368, 604/365.01, 385.101, 385.16, 385.21, 385.23

(56) References Cited

U.S. PATENT DOCUMENTS

| | | |
|---|---|---|
| 3,717,150 A | 2/1973 | Schwartz |
| 3,901,236 A | 8/1975 | Assarsson et al. .......... 128/284 |
| 4,076,663 A | 2/1978 | Masuda et al. ....... 260/17.4 GC |
| 4,259,387 A | 3/1981 | Mesek ........................ 428/167 |
| 4,286,082 A | 8/1981 | Tsubakimoto et al. ...... 526/240 |
| 4,847,134 A | 7/1989 | Fahrenkrug et al. ........ 428/138 |
| 4,965,122 A | 10/1990 | Morman ..................... 428/225 |
| 5,114,781 A | 5/1992 | Morman ..................... 428/198 |
| 5,116,662 A * | 5/1992 | Morman ..................... 428/128 |
| 5,364,382 A | 11/1994 | Latimer et al. .............. 604/378 |
| 5,366,452 A | 11/1994 | Widlund et al. ......... 604/385.2 |
| 5,376,198 A | 12/1994 | Fahrenkrug et al. ........ 156/164 |
| 5,389,095 A | 2/1995 | Suzuki et al. ............ 604/385.2 |
| 5,411,497 A | 5/1995 | Tanzer et al. ............... 604/368 |
| 5,425,725 A | 6/1995 | Tanzer et al. ............... 604/368 |
| 5,433,715 A | 7/1995 | Tanzer et al. ............... 604/368 |
| 5,451,219 A * | 9/1995 | Suzuki et al. ............ 604/385.2 |
| 5,509,915 A | 4/1996 | Hanson et al. .............. 604/378 |
| 5,520,673 A | 5/1996 | Yarbrough et al. ......... 604/378 |
| 5,560,878 A | 10/1996 | Dragoo et al. .............. 264/115 |
| 5,593,399 A | 1/1997 | Tanzer et al. ............... 604/368 |
| 5,601,542 A * | 2/1997 | Melius et al. ............... 604/368 |
| 5,611,790 A * | 3/1997 | Osborn, III et al. ........ 604/391 |
| 5,645,542 A | 7/1997 | Anjur et al. ................. 604/368 |
| 5,662,634 A | 9/1997 | Yamamoto et al. ......... 604/378 |
| 5,683,374 A | 11/1997 | Yamamoto et al. ...... 604/385.2 |
| 5,824,004 A | 10/1998 | Osborn, III et al. ..... 604/385.2 |
| 5,846,232 A | 12/1998 | Serbiak et al. |
| 5,883,028 A | 3/1999 | Morman et al. ............ 442/394 |
| 5,928,211 A | 7/1999 | Gustafsson et al. |

FOREIGN PATENT DOCUMENTS

| | | | |
|---|---|---|---|
| EP | 0 591 647 A2 | 4/1994 | |
| EP | 0 650 714 A1 | 5/1995 | |
| WO | 96/16624 | 6/1996 | ........... A61F/13/15 |
| WO | 97/01996 | 1/1997 | |
| WO | 98/37846 | 9/1998 | |
| WO | 99/00095 | 1/1999 | |

* cited by examiner

Primary Examiner—Aaron J. Lewis
Assistant Examiner—Jamisue A Webb
(74) Attorney, Agent, or Firm—Pauley Petersen Kinne & Erickson

(57) ABSTRACT

An absorbent article is provided with a central region which is selectively stretchable in the longitudinal direction, and two end regions adjacent to the central region which are selectively stretchable in the lateral direction. When employed as a garment, such as a disposable diaper or pant-like absorbent garment, the central region provides selective longitudinal (front-to-back) stretching in the crotch area of the wearer, and the two end regions provide selective lateral (side-to-side) stretching in the front and back waist areas of the wearer.

32 Claims, 5 Drawing Sheets

ABSORBENT ARTICLE HAVING ZONED DIRECTIONAL STRETCHING

FIELD OF THE INVENTION

This invention is directed to an absorbent article having longitudinal stretchability in a central region and lateral stretchability in two end regions.

BACKGROUND OF THE INVENTION

It is known to make absorbent articles, such as disposable diapers and pant-like absorbent garments, using stretchable materials. Some absorbent articles are rendered stretchable by placing elastic bands in the waist and leg regions, and otherwise employing inelastic construction materials. In some instances, absorbent articles have employed elastic or otherwise stretchable materials in constructing the primary layers. This approach has been limited because most absorbent articles include, at minimum, a liquid-permeable top layer, an absorbent core composite, and a substantially liquid impermeable outer cover material. The use of an elastic or stretchable material in one or more layers will not render the absorbent article stretchable unless each and every layer can be made from a similarly stretchable material. Often, the absorbent composite in the core is the least stretchable of the layers, and tears when the top layer and outer cover materials can be stretched to a greater degree.

Stretchable absorbent articles are disclosed, for instance in U.S. Pat. No. 5,560,878, issued to Dragoo et al., and in U.S. Pat. No. 5,645,542, issued to Anjur et al. In the disclosed articles, all of the layers are stretchable. Other stretchable absorbent articles are disclosed in U.S. Pat. No. 4,847,134 and 5,376,198, both issued to Fahrenkrug et al. In these articles, some of the layers are more stretchable than others. The less stretchable layers form rugosites upon relaxation.

During actual use of absorbent articles, such as disposable diapers and pant-like absorbent garments, there is a greater need for a lateral stretch in the waist regions, and a greater need for a longitudinal stretch in the central "crotch" region. Absorbent articles which stretch uniformly in all directions at all locations will accommodate the desired stretching, but will also stretch in directions and regions where no stretching is desired. There is a need or desire for an absorbent article which stretches only in selected directions in selected regions, as needed.

SUMMARY OF THE INVENTION

The present invention is directed to an absorbent article having a central region between two end regions. The absorbent article is selectively stretchable in a longitudinal direction in the central region, and is selectively stretchable in a lateral direction (i.e., a direction substantially perpendicular to the longitudinal direction) in the two end regions. The absorbent article is particularly suitable for diapers and pant-like absorbent garments, where lateral stretching in the waist regions and longitudinal stretching in the crotch region are desirable. The absorbent article is also suitable for use in any other absorbent application where these selective stretching properties are desired.

With the foregoing in mind, it is a feature and advantage of the invention to provide an absorbent article having selective stretching in different regions, wherein the degree and direction of stretching correspond to parameters which are ideal for each region.

It is also a feature and advantage of the invention to provide a disposable diaper that is selectively stretchable longitudinally in the central region, and laterally in the two end regions.

It is also a feature and advantage of the invention to provide a pant-like absorbent garment that is selectively stretchable longitudinally in the central region, and laterally in the two end regions.

The foregoing and other features and advantages will become further apparent from the following detailed description of the presently preferred embodiments, read in conjunction with the drawings.

DETAILED DESCRIPTION OF THE PRESENTLY PREFERRED EMBODIMENTS

The present invention is an absorbent article having a central region and two end regions. The absorbent article is selectively stretchable in the longitudinal direction in the central region, and in the lateral direction in the two end regions.

As used herein, the term "selectively stretchable" means that a material is more stretchable in a first direction than in a second direction, that is, can be stretched to a greater degree without rupture of the overall material in the first direction than in the second direction. Individual filaments, layers or bonds may break without rupturing the overall material. The second direction is perpendicular to the first direction. Generally, the material is stretchable to at least 150% its initial length in the first direction, suitably to at least about 200% of its initial length in the first direction, desirably to at least about 250% of its initial length in the first direction. Generally, the material is stretchable to less than 140% of its initial length in the second direction, suitably to less than about 125% of its initial length in the second direction, desirably to less than about 110% of its initial length in the second direction.

Figure 2:
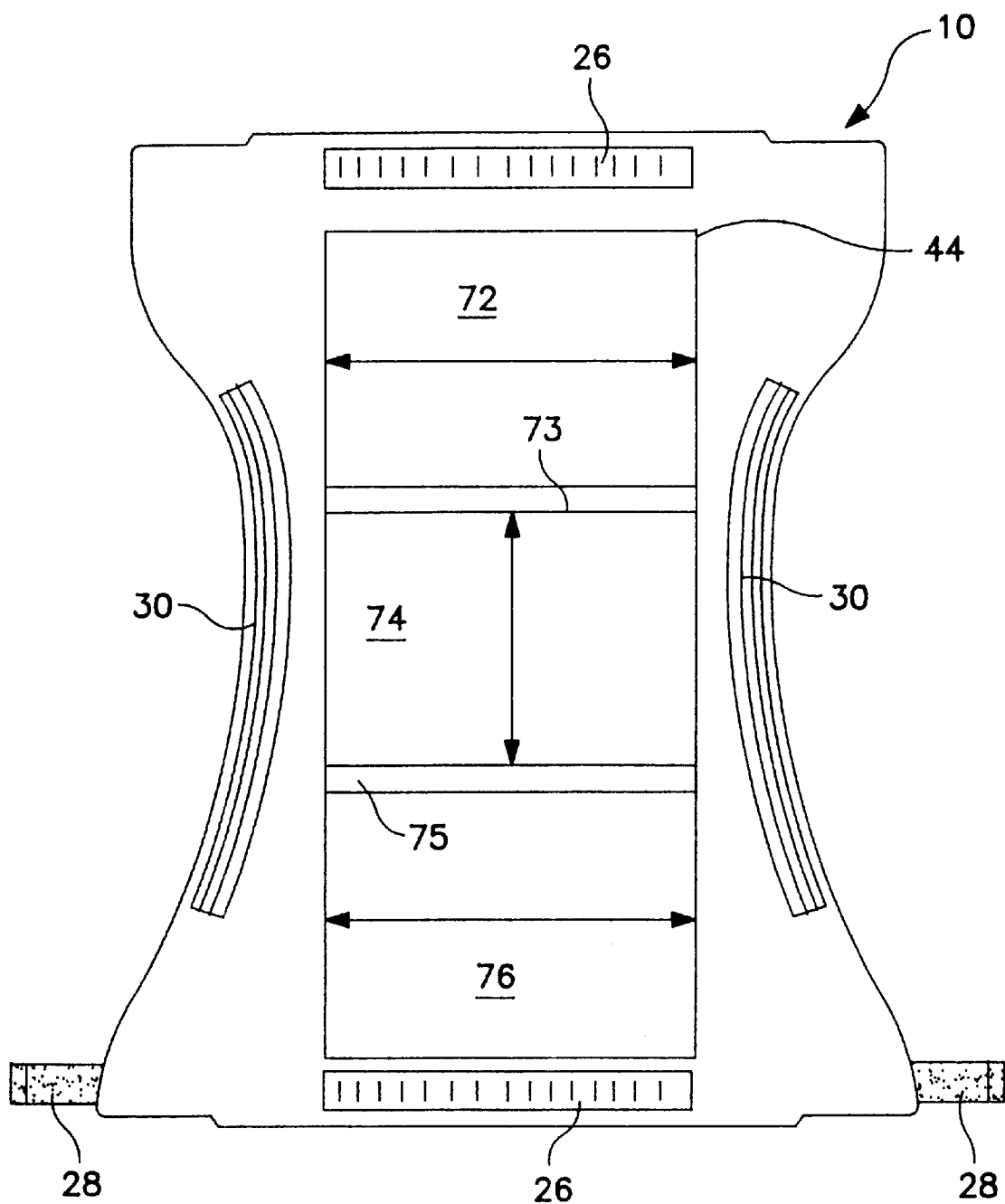
FIG. 2 is a cut away plan view of the diaper showing an absorbent core composite useful in an absorbent article of the invention.

As used herein, the terms "longitudinal direction" and "lateral direction" are defined with respect to an absorbent article laid out flat as shown in FIG. 2. The longitudinal direction is any direction of stretch which can be represented by a straight line passing through the central region, and at least a portion of both end regions, of the absorbent garment. The lateral direction is any direction of stretch which cannot be represented by a straight line passing through the central region, and at least a portion of both end regions, of the absorbent garment. The boundary between the central region and an end region is where the transition occurs from selective stretchability in a first direction, to selective stretchability in a second direction.

As used herein, the term "absorbent article" includes without limitation diapers, training pants, swim wear, absorbent underpants, adult incontinence products, feminine hygiene products and medical absorbent products (for example, absorbent medical garments, underpads, bandages, drapes, and medical wipes).

Figure 1:
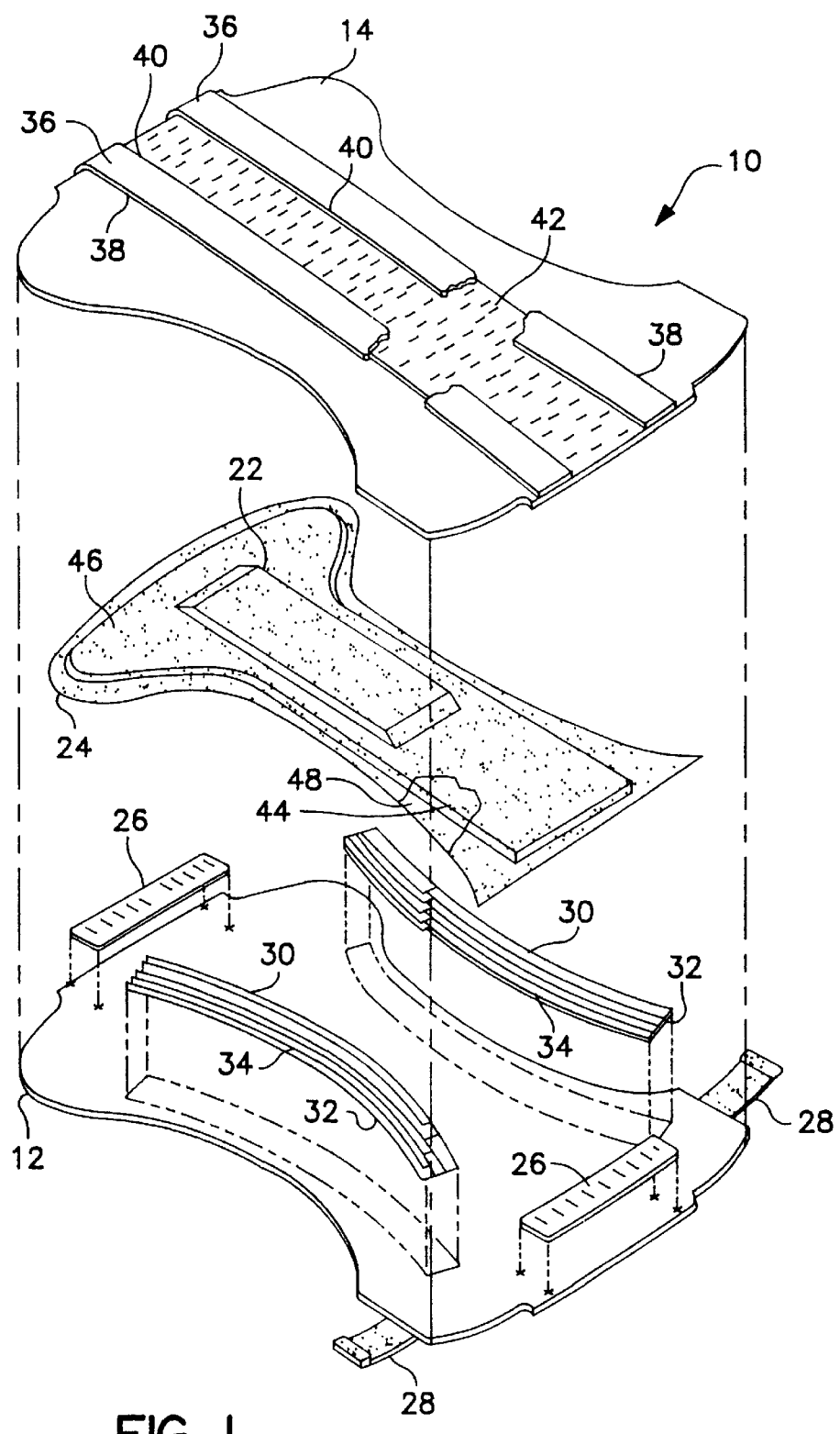
FIG. 1 is an exploded perspective view of a diaper according to the invention.

One preferred absorbent article is a disposable diaper. FIG. 1 illustrates an exploded perspective view of a disposable diaper according to one embodiment of the present invention. Disposable diaper 10 includes an outer cover 12, a body-side liner 14, and an absorbent composite 44 located between the body-side liner 14 and the outer cover 12. The absorbent composite 44 comprises a plurality of pockets containing a superabsorbent material and, optionally, wood pulp fibers as further described below. The absorbent composite also includes a two-piece wrap sheet comprising upper wrap sheet layer 46 and lower wrap sheet layer 48 described further below. The absorbent composite 44 has a profiled thickness to define an area 22 of increased basis weight. The two-piece wrap sheet extends beyond the edges of the absorbent composite 44 to define perimeter 24 which can be sealed to prevent superabsorbent material from migrating out of the diaper.

Attached to outer cover 12 are waist elastics 26, fastening tapes 28 and leg elastics 30. The leg elastics 30 comprise a carrier sheet 32 and individual elastic strands 34.

The body-side liner 14 includes containment flaps 36 having proximal edges 38 and distal edges 40. A surge management layer 42 is located between the proximal edges 38 of the containment flaps 36.

The exact construction method and materials of the diaper illustrated in FIG. 1 is set forth in greater detail in commonly assigned U.S. Pat. No. 5,509,915, issued Apr. 25, 1996 in the name of Hanson et al., incorporated herein by reference. Possible modifications to the diaper illustrated in FIG. 1 are set forth in commonly assigned U.S. Pat. No. 5,509,915 referenced above and in commonly assigned U.S. Pat. No. 5,364,382, issued Nov. 15, 1994 in the name of Latimer et al. Such possible modifications include positioning the surge management layer 42 between the body-side liner 14 and the absorbent composite 44 and reducing the length of the surge management layer to extend the length of the absorbent composite or massing (reduce length and increase basis weight) the surge management layer in the area of the diaper where liquid waste initially accumulates (target zone).

To make a zoned, selectively stretchable absorbent article according to the invention, any one or more of the outer cover 12, body side liner 14, and absorbent composite 44 may have the regional, selective stretchability described above. The remaining layers may be selectively stretchable in the same regions and directions, may be uniformly stretchable in all directions, or may be elastic. An elastic material is a stretchable material which, when relaxed after stretching, recovers or "retracts" most of the way to its initial, pre-stretched length.

FIG. 2 illustrates one embodiment of the invention, in which the absorbent composite 44 has regional, selective stretchability. Absorbent composite 44 includes a first end region 72, a central region 74, and a second end region 76. End regions 72 and 76 are joined to central region 74 along seams 73 and 75. End regions 72 and 76 are selectively stretchable in the lateral direction, and central region 74 is selectively stretchable in the longitudinal direction, as shown by the respective arrows. Each of the regions 72, 74 and 76 should constitute about 20–60% of the longitudinal length of the absorbent article, preferably about 25–50% of the length, more preferably about 30–40% of the length.

Figure 3:
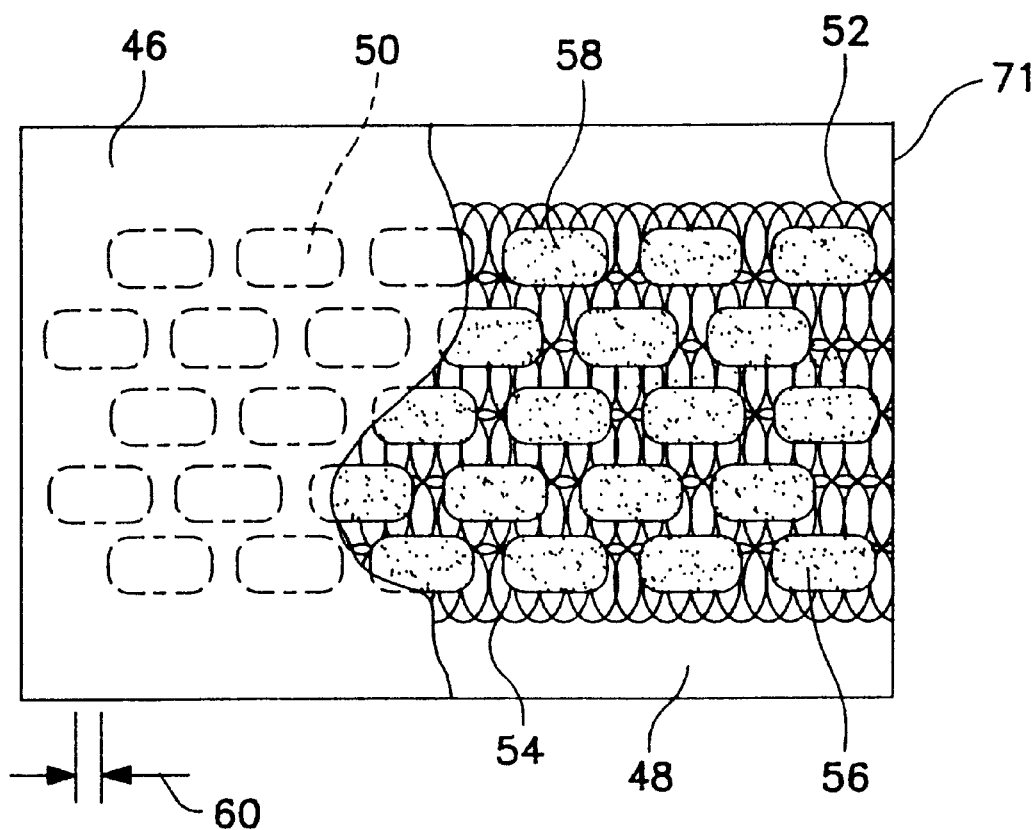
FIG. 3 is a cut away plan view of one section of the absorbent core composite.

FIG. 3 illustrates a selectively stretchable absorbent composite section 71 useful in the central region 74 and/or end regions 72 and 76. The section 71 of absorbent composite 44 comprises a selectively stretchable liquid permeable first substrate layer 46, a selectively stretchable second substrate layer 48 and pockets 50 of superabsorbent material formed between the first layer 46 and second layer 48. The pockets 50 are defined by attachment means 52 which serve to operatively join the first and second layers to form a laminate and to maintain the integrity of the laminate when the laminate is dry but to release when the laminate becomes wetted. Alternatively, pockets 50 may be molded (e.g. thermoformed) into layer 46 or layer 48. Suitable attachment means between layers 46 and 48 include water sensitive adhesives, such as water soluble adhesives and thermal embossing. The attachment means 52 secures together the first layer 46 and the second layer 48 to provide attached zones 54 and unattached zones 56. The unattached zones define pockets 50. A superabsorbent material 58 is located in the unattached zones 56 (and hence, in pockets 50). In addition to the superabsorbent material 58, the pockets 50 may contain a fibrous material such as cellulose fluff or another material, as discussed further below.

The pockets 50 are spaced by a distance 60 when the section 71 is relaxed, i.e., is not subject to a stretching force. The spacing 60 is at least about 0.05 inch (1.3 mm), alternatively at least about 0.10 inch (2.5 mm) or alternatively at least about 0.15 inch (3.8 mm). Moreover, the pocket spacing 60 is suitably not more than about 1.5 inch (38 mm), alternatively not more than about 1.0 inch (25 mm), or alternatively not more than about 0.5 inch (13 mm).

The depth of pockets 50 may be at least about 0.1 inch (2.5 mm), preferably about 0.15–0.50 inch (3.8–13 mm), more preferably about 0.20–0.30 inch (5.1–7.6 mm). The pockets may have a circular or elliptical configuration, with diameters ranging from about 0.20–1.0 inch (5.1–25 mm), preferably about 0.25–0.75 inch (6.4–19.1 mm), more preferably about 0.40–0.60 inch (10.2–15.2 mm). These dimensions refer to the relaxed, unstretched state of absorbent composite section 71.

In accordance with the invention, the section 71 should be stretchable in a first direction, and not stretchable in a second direction perpendicular to the first direction. By "stretchable" it is meant that the section 71 stretches to at least 150% of its initial length in the first direction without breaking, preferably to at least 200% of its initial length, more preferably to at least 250% of its initial length. Preferably, the absorbent section 71 is at least partially retractable in the direction opposite to the direction of stretching. Thus, when the force causing the stretching is relaxed, the stretched composite should recover or "retract" by at least 25%, preferably by at least 50%, more preferably by at least 75%. A "50% recovery", for example, means that when a material is stretched from an initial length of one meter to a stretched length of two meters, it should recover to a length of 1.5 meters when the stretching force is removed. The stretchability of absorbent composite section 71 is generally controlled by the stretchability of the combined substrate layer or layers 46 and 48.

The absorbent composite section 71 is oriented in the absorbent article so that the direction of selective stretching corresponds to a direction where that region of the article may desirably be stretched. In the central region 74 of a diaper, for instance, the direction of preferred stretching is longitudinal, toward the front and back of the diaper. In the end regions 72 and 76 of a diaper, the direction of preferred stretching is lateral. Absorbent composite 44 (FIG. 2) can thus be prepared from three absorbent sections 71, joined together at their edges. Absorbent section 71 for the central region 74 can be oriented so that its direction of preferred stretching is longitudinal. Absorbent sections 71 for end regions 72 and 76 can be oriented perpendicular to section 71 in the central region, so that the end regions 72 have a preferred direction of stretch that is lateral.

Figure 4A:
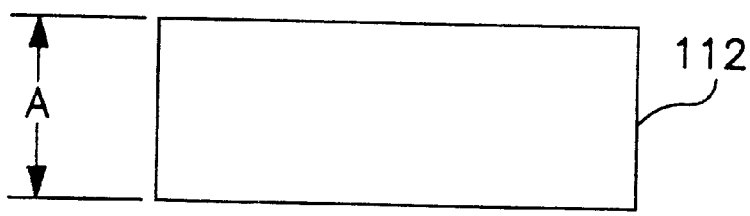
FIGS. 4A, 4B and 4C schematically illustrate the formation of a neck-bonded laminate useful as a substrate in the absorbent core composite.
Figure 4B:
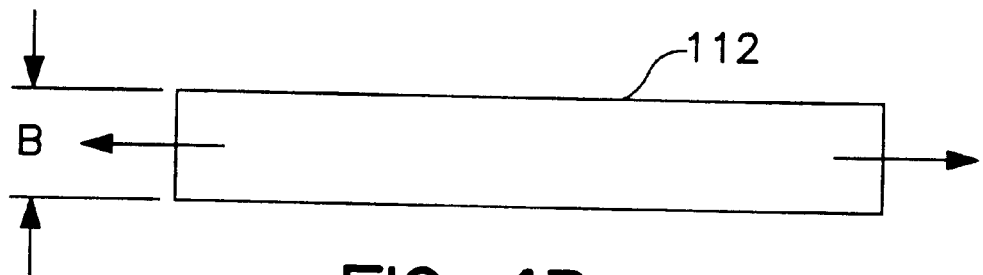
Figure 4C:
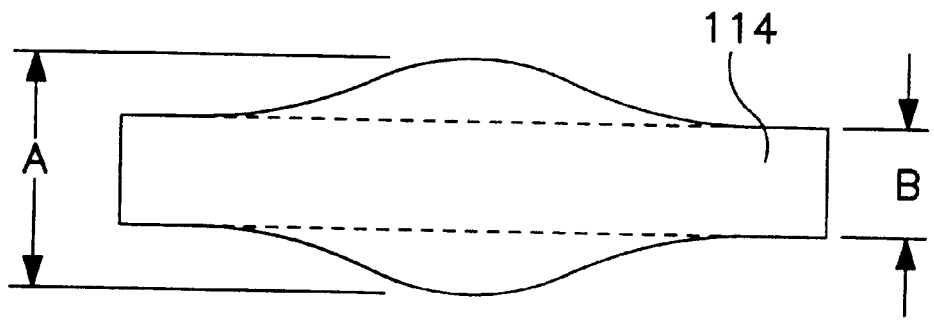

FIGS. 4, 4A and 4B illustrate the formation of a neck-bonded laminate which may be employed as the first substrate layer 46 and/or the second substrate layer 48 of sections 71 of the absorbent composite 44. FIG. 4 illustrates a neckable material 112 which can, for instance, be a fibrous nonwoven web made of a relatively inelastic polymer material. Referring to FIG. 4B, the neckable material 112 is first pulled in a machine direction, causing its fibers to longitudinally orient and causing its length in the cross direction to contract from a first dimension "A" to a second dimension "B". At that point, the neckable nonwoven web 112 is laminated to an unstretched elastic film or other layer material, for instance using techniques described in U.S. Pat. No. 5,883,028, issued to Morman et al., which is incorporated by reference. The term "elastic" refers to a stretchable material which mostly recovers to its initial length when a stretching force is relaxed.

The resulting laminate 114, shown in FIG. 4B, has a relaxed length in the cross-machine direction which is substantially equal to the dimension "B". The laminate can be selectively stretched only in the cross-machine direction of the web 112, to a second length substantially equal to the dimension "A". When the stretching force is relaxed, the laminate 114 retracts to its original dimension "A".

The neckable web 112 may be a porous nonwoven material such as, for example, spunbonded web, meltblown web or bonded carded web. If the neckable material is a web of meltblown fibers, it may include meltblown microfibers. The neckable material 112 may be made of fiber forming polymers such as, for example, polyolefins. Exemplary polyolefins include one or more of polypropylene, polyethylene, ethylene copolymers, propylene copolymers, and butene copolymers. Useful polypropylenes include, for example, polypropylene available from the Exxon Chemical Company under the trade designation Exxon 3445, and polypropylene available from Shell Chemical Company under the trade designation DX 5A09.

The neckable web 112 may be a multilayer material having, for example, at least one layer of spunbonded web joined to at least one layer of meltblown web, bonded carded web or other suitable material. For example, neckable material 112 may be a multilayer material having a first layer of spunbonded polypropylene having a basis weight from about 0.2 to about 8 ounces per square yard (osy) (about 6.8–270 grams/m$^2$, or gsm), a layer of meltblown polypropylene having a basis weight from about 0.2 to about 4 osy (6.8–135 gsm), and a second layer of spunbonded polypropylene having a basis weight of about 0.2 to about 8 osy (6.8–270 gsm). Alternatively, the neckable web 112 may be a single layer of material such as, for example, a spunbonded web having a basis weight of from about 0.2 to about 10 osy (6.8–340 gsm) or a meltblown web having a basis weight of from about 0.2 to about 8 osy (6.8–270 gsm). The adjacent fibers of web 112 should be intermittently joined by interfiber bonding, using conventional techniques known in the art.

An elastic sheet may be joined to the neckable web 112 when the latter is in the tensioned, necked state to form the neck-bonded laminate 114. The elastic sheet may be made from a water vapor permeable elastic polymer, or may be made from another elastic polymer and rendered vapor permeable by forming apertures or micropores in the sheet. Preferably, the elastic sheet has a moisture vapor transmission rate (MVTR) of at least about 500 grams/m$^2$-24 hours, more preferably at least about 1200 grams/m$^2$-24 hours, most preferably at least about 2000 grams/m$^2$-24 hours using the test procedure described below. The MVTR is a function of both film thickness and polymer type. Elastic polymers which exhibit the required MVTR over a range of useful film thicknesses include without limitation vulcanized silicone rubber, some other silicone polymers, polyurethanes, polyether esters and polyether amides. The following Table 1 gives representative water vapor permeabilities of exemplary elastic polymers which have been normalized to account for film thickness of a solid (nonporous) polymer film.

TABLE 1

| Polymer Type | Water Vapor Permeability, kg-cm/(km)$^2$-day |
| --- | --- |
| Vulcanized silicone rubber | 11,900 |
| Polyurethane-Estane ® 58237 | 760 |
| Polyurethane-Estane ® 58245 | 1,270 |
| Polyether amide-PEBAX ® | 830 |
| Polyether ester Hytrel ® or Arnitel ® | 930 |
| Polyester-polyurethane copolymer | 160 |
| Polyether-polyurethane copolymer | 310 |

If the elastic polymer has low water vapor permeability, the film may have to be extremely thin in order to achieve the desired minimum level of MVTR. Elastomers having lower vapor permeability include, for instance, styrene-butadiene copolymers and terpolymers, elastomeric ethylene-propylene copolymers, ethylene-propylene-diene rubbers, and certain single-site or metallocene-catalyzed ethylene polymers and ethylene-alpha olefin copolymers having a density not exceeding 0.89 grams/cc. Alternatively, the film may be rendered porous or microporous using numerous techniques familiar to persons skilled in the art. The production and use of very thin films may be impractical due to low film strength and processing difficulties. The elastic polymer itself should therefore have sufficient water vapor permeability to allow the use of films having practical thicknesses. Preferably, the elastic polymer will have a water vapor permeability of at least about 150 kg-cm/(km)$^2$-day, more preferably at least about 500 kg-cm/(km)$^2$-day, most preferably at least about 1000 kg-cm/(km)$^2$-day.

In addition to being water vapor permeable, the preferred breathable elastic film should not be so thick as to substantially impair its water vapor transmission. The MVTR of a particular composition of film is roughly inversely related to its thickness if there are no molecular interactions between the film and the vapor. For water vapor permeable films, this relationship may vary due to the affinity of the water with the films. Generally, the elastic film component of neck-bonded laminate 114 should be less than about 2 mils (50 microns) thick, preferably less than about 1 mil (25 microns) thick, more preferably less than about 0.5 mil (13 microns) thick, when the film and laminate 114 are relaxed.

Referring to FIG. 2, when a neck-bonded laminate is used as the substrate in absorbent composite 44, the top (liquid permeable) layer 46, which faces the wearer, may be a reversibly necked, nonwoven layer and the bottom layer 48 may be an elastic film or sheet, of the neck-bonded laminate. Reversibly necked nonwovens are described in U.S. Pat. No. 4,965,122, issued to Morman, which is incorporated by reference. Alternatively, the bottom layer 48 may include an entire neck-bonded laminate (film and necked nonwoven web), and the top layer 46 may be another nonwoven or other liquid-pervious layer, such as a nonwoven spunbond layer. The layers 46 and 48 may be bonded together using a wide variety of conventional techniques, including adhesive bonding, thermal bonding, ultrasonic bonding and the like. Preferably, the bonded area constitutes about 10–20% of the interface between layers 46 and 48. In one preferred embodiment, a stretchable hot melt adhesive 2525A available from Findlay Adhesives Co. is applied in a swirl pattern covering 10–20% of the interface.

Pockets 50 may be formed in layer 46 or layer 48, and are preferably formed in bottom layer 48. Pockets 50 may be formed using a vacuum thermoforming process or another suitable process. In one embodiment, the pocket forming, superabsorbent application and bonding are performed in an integrated process. Initially, a selectively stretchable material 46 such as a neck-stretched spunbond material, is positioned over a perforated plate having pocket-shaped depressions. Vacuum is applied to the plate, causing the material to be pulled into pocket-shaped depressions. A superabsorbent is then added to each pocket, and an adhesive is applied to layer 46. Then, second (top) layer 48, which is liquid pervious, is positioned over layer 46 and its pockets, and pressed. The layers 46 and 48 are thus bonded by action of the adhesive.

The term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride. The superabsorbent materials can be natural, synthetic, and modified natural polymers and materials. In addition, the superabsorbent materials can be inorganic materials, such as silica gel, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations of Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrile-grafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. No. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbents may be particulate or fibrous, and are preferably particulate. Superabsorbents are generally available in particle sizes ranging from about 20 to about 1000 microns. Examples of commercially available particulate superabsorbents include SANWET® IM 3900 and SANWET® IM-5000P, available from Hoescht Celanese located in Portsmouth, Virginia, DRYTECH® 2035LD available from Dow Chemical Co. located in Midland, Michigan, and FAVOR® 880 available from Stockhausen, located in Sweden. FAVOR® 880 is presently preferred because of its high gel strength. An example of a fibrous superabsorbent is OASIS® 101, available from Technical Absorbents, located in Grimsby, United Kingdom.

Depending on the size of pockets 50, and density of the superabsorbent, each pocket may contain about 25–500 mg of superabsorbent material, based on its dry weight, preferably about 50–300 mg, more preferably about 100–200 mg. The number and size of pockets 50 may be such that selectively stretchable absorbent composite 44 contains about 1–100 grams of total superabsorbent, preferably about 3–50 grams, more preferably about 5–15 grams. Of course, the total amount of superabsorbent may vary depending on the size of the absorbent article.

In addition to the superabsorbent material, each pocket 50 may contain, if desired, a fibrous absorbent material such as pulp fibers, a filler material, an odor absorbent material, a fragrant material, or another suitable material. When combinations of materials are employed, the superabsorbent should constitute at least 30% of the total material in pockets 50, preferably at least 50%, more preferably at least 70%, most preferably at least 90%. The selective stretchability of each of the absorbent composite sections 71 permits a high concentration of superabsorbent to be contained in pockets 50, without resulting in gel blocking, when the composite becomes wet. As the superabsorbent becomes wet and the pockets expand toward each other, the selective stretchability of each composite section 71 permits movement of the pockets, thus preventing their contact from becoming so tight that gel blocking occurs.

Preferably, the pockets 50 have a shape which permits them to touch each other without closing all of the space between them. When viewed in plan, as in FIG. 3, pockets 50 have a circular, oval or elliptical shape. Square and rectangular shapes are less preferred, because these shapes would permit substantially continuous contact along the edges of adjacent pockets 50.

The absorbent composite sections 71, forming regions 72, 74 and 76 of absorbent composite 44 (FIG. 2) may be joined at their edges using thermal bonding, ultrasonic bonding, mechanical stitch bonding, adhesive bonding, or any other suitable techniques. The same variety of bonding techniques may be employed to join the outer cover 12, body side liner 14, and absorbent composite 44 (FIG. 1) to form a unitary diaper structure. In order to achieve optimum performance, it is desired that the selective stretchability of the different regions of the absorbent composite 44, be allowed to control the stretchability of the entire diaper 10. This can be accomplished by forming the other layers of the diaper 10 from materials that are at least as stretchable as the regions 72, 74 and 76 of the absorbent composite 44. The body side liner 14 and outer cover 12 need not be selectively stretchable. They can be uniformly stretchable in all directions, and can be formed using one or more of the elastic polymers described above. As long as one of the layers (e.g., the absorbent core) has the desired zoned, selective stretchability, and the remaining layers are at least as stretchable, the stretching properties of the entire diaper 10 will be governed by the stretchability of the layer having the zoned, selective stretch properties.

Other embodiments of the invention may achieve the same result. For instance, the layer having the desired zoned, longitudinal stretchability in the central region and the lateral stretchability in the two end regions may be the body side liner 14 and/or the outer cover 12. Whichever layer has the zoned, selective stretchability, it is preferred that the other layers be at least as stretchable so that the entire diaper can be selectively stretchable longitudinally in the central region, and laterally in the two end regions.

Both the surge layer 42 and the body side liner 14 are constructed from highly liquid pervious materials. These layers function to transfer liquid from the wearer to the absorbent composite 44. Suitable materials include porous woven materials, porous nonwoven materials, and apertured films. Examples include, without limitation, any stretchable porous sheets of polymeric fibers, bonded carded webs of synthetic or natural fibers or combinations thereof. Either layer may also be an apertured stretchable plastic film.

The outer cover 12 may include a single stretchable layer, or may include multiple stretchable layers joined together by adhesive bonding, thermal bonding, ultrasonic bonding or the like. Outer cover 12 can be made from a wide variety of woven or nonwoven material, films, or a film-coated nonwoven material, including, for instance, cast or blown films. Outer cover 12 may also be a composite of a bonded carded or spunbonded or meltblown material, for example, a spunbonded-meltblown-composite of thermoplastic material or a spunbonded-meltblown-spunbonded thermoplastic material, wherein the spunbonded layer can provide a cloth-like texture and the meltblown layer can provide liquid impermeability. Outer cover 12 is preferably highly breathable to water vapor.

Figure 5:
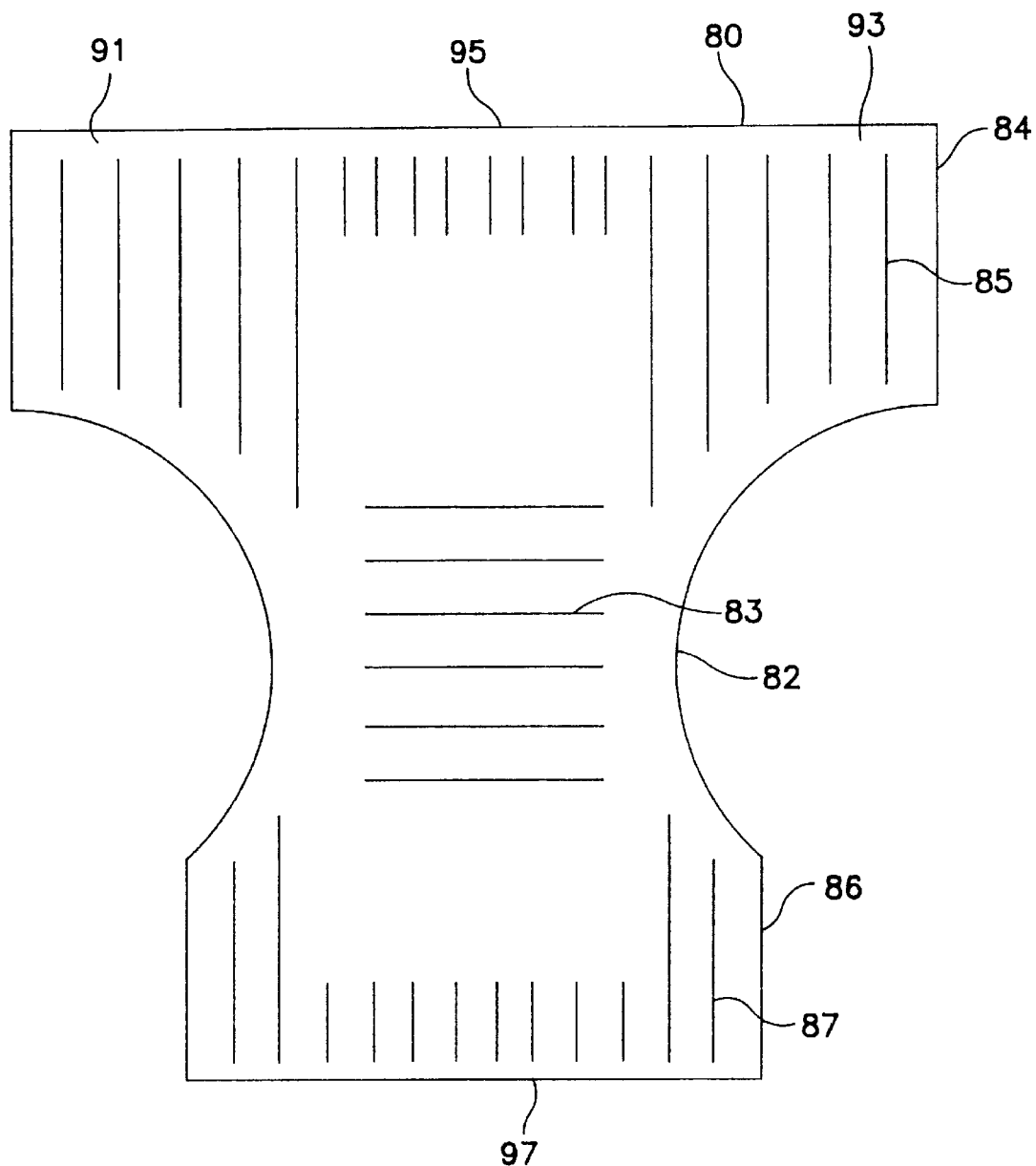
FIG. 5 illustrates another technique for forming a diaper according to the invention.

FIG. 5 illustrates another technology for forming an absorbent article having zoned directional stretching. The material 80 shown in FIG. 5 may, for instance, be an outer cover material or a body side liner in a diaper. The material 80 can have one or more layers, and is formed from a precursor material which is biaxially stretchable (stretchable in both the longitudinal and lateral directions) and which may be elastomeric. For instance, the precursor material may be an elastomeric nonwoven web, a laminate of an elastic nonwoven web and an elastic film, or a necked stretched bonded nonwoven laminate (NSBL) material. An NSBL material may include an elastic sheet thermally or adhesively bonded at spaced apart locations to a neckable nonwoven (e.g. spunbond) web when the nonwoven web is necked in a first direction and the elastic sheet is stretched in a second direction perpendicular to the first direction. The NSBL has stretchability in the first direction due to the necking of the web, and in the second direction due to the rugosites formed in the web when the elastic sheet is relaxed. Processes for making a multidirectional stretchable laminate from an elastic sheet and a necked nonwoven web are described in U.S. Pat. Nos. 5,116,662 and 5,114,781, both issued to Morman, the disclosures of which are incorporated by reference.

The material 80 is a single-piece material having a central region 82 and two end regions 84 and 86. Central region 82 is rendered selectively stretchable in the longitudinal direction by imparting a plurality of bond lines 83 oriented in the lateral direction, which inhibit stretching in the lateral direction but have little impact on stretchability in the longitudinal direction. End regions 84 and 86 are rendered selectively stretchable in the lateral direction by imparting a plurality of bond lines 85 and 87 oriented in the longitudinal direction, which inhibit stretching in the longitudinal direction but have little impact on stretchability in the lateral direction.

A thermal calender bonding process known to persons skilled in the art may be used to apply the bond lines 83, 85 and 87 to the material 80. Other bonding procedures may also be used, including other thermal bonding processes, adhesive bonding, and/or ultrasonic welding. The application of bond lines to the elastic nonwoven web (or nonwoven web component of an elastic laminate) results in a material 80 having regions of higher extensibility in a direction where there is a lower level of interfilament bonding, and regions of lower extensibility in a direction where there is a higher level of interfilament bonding. This means that stretchability of a given region is significantly reduced in a direction parallel to the orientation of the bond lines, and only nominally reduced in a direction perpendicular to the orientation of the bond lines. The applied bond lines impart additional localized interfilament bonding and interlayer bonding, beyond that which already exists from the manufacture of the nonwoven web and/or laminate.

The length, thickness and frequency of bond lines influences how much the stretchability of a material is reduced in regions affected by the bond lines. Referring to FIG. 5, end regions 84 and 86 have bond lines 85 of greater length in the leg regions 91 and 93, than in the front region 95 and back region 97. The longer bond lines in leg regions 91 and 93 ensure a tighter fit of the garment around the legs of the wearer, by substantially reducing or eliminating longitudinal stretchability in the leg regions. The shorter bond lines in the front and back regions 95 and 97 impart a correspondingly lower reduction in longitudinal stretchability in these regions. Thus, the bond lines can be used to control both the direction and degree of selected stretchability in the various regions of material 80. A more thorough description of the selective bonding technology is provided in U.S. patent application Ser. No. 09/346,665, filed on Jun. 30, 1999 in the name of Morman et al., entitled "Variable Stretch Material And Process To Make It," the disclosure of which is incorporated by reference.

Test Procedure For Measuring Moisture Vapor Transmission Rate (MVTR)

A measure of the breathability of a fabric is the moisture vapor transmission rate (MVTR), which for the sample materials is calculated essentially in accordance with ASTM Standard E96–80 with minor variations in test procedure as set forth below. Circular samples measuring three inches in diameter are cut from each of the test materials, and tested along with a control which is a piece of CELGARD® 2500 sheet from Celanese Separation Products of Charlotte, North Carolina. CELGARD® 2500 sheet is a microporous polypropylene sheet. Three samples are prepared for each material. The test dish is a number 60-1 Vapometer pan distributed by Thwing-Albert Instrument Company of Philadelphia, Pa. One hundred milliliters of water is poured into each Vapometer pan and individual samples of the test materials and control material are placed across the open tops of the individual pans. Screw-on flanges are tightened to form a seal along the edges of the pan, leaving the associated test material or control material exposed to the ambient atmosphere over a 6.5 centimeter diameter circle having an exposed area of approximately 33.17 square centimeters. The pans are placed in a forced air oven at 100° F. (32° C.) for 1 hour to equilibrate. The oven is a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans are removed from the oven, weighed and immediately returned to the oven. After 24 hours, the pans are removed from the oven and weighed again. The preliminary test water vapor transmission rate values are calculated as follows:

Test MVTR=(grams weight loss over 24 hours)×315.5 g/m²-24 hours

The relative humidity within the oven is not specifically controlled.

Under predetermined set conditions of 100° F. (32° C.) and ambient relative humidity, the MVTR for the CELGARD® 2500 control has been defined to be 5000 grams per square meter for 24 hours. Accordingly, the control sample is run with each test and the preliminary test values are corrected to set conditions using the following equation:

MVTR=(Test MVTR/control MVTR)×(5000 g/m²-24 hours)

While the embodiments disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

We claim:

1. An absorbent article, comprising:
   a central region including a neck-bonded laminate formed by laminating a necked nonwoven web to an unstretched elastic film; and
   two end regions on opposite sides of the central region, each end region including a neck-bonded laminate formed by laminating a necked nonwoven web to an unstretched elastic film;
   wherein each of the central region and two end regions has an initial length in the longitudinal direction and an initial length in the lateral direction;
   the central region is stretchable to at least 150% of its initial length in the longitudinal direction and only to less than 140% of its initial length in the lateral direction; and
   each of the two end regions is stretchable to at least 150% of its initial length in the lateral direction and only to less than 140% of its initial length in the longitudinal direction.

2. The absorbent article of claim 1, wherein the central region is stretchable to at least 200% of its initial length in the longitudinal direction.

3. The absorbent article of claim 1, wherein the central region is stretchable to at least 250% of its initial length in the longitudinal direction.

4. The absorbent article of claim 1, wherein the central region is stretchable to less than 125% of its initial length in the lateral direction.

5. The absorbent article of claim 1, wherein the central region is stretchable to less than 110% of its initial length in the lateral direction.

6. The absorbent article of claim 1, wherein each of the end regions is stretchable to at least 200% of its initial length in the lateral direction.

7. The absorbent article of claim 1, wherein each of the end regions is stretchable to at least 250% of its initial length in the lateral direction.

8. The absorbent article of claim 1, wherein each of the end regions is stretchable only to less than 125% of its initial length in the lateral direction.

9. The absorbent article of claim 1, wherein each of the end regions is stretchable only to less than 110% of its initial length in the lateral direction.

10. An absorbent article, comprising:
    a liquid-permeable body side liner;
    a substantially liquid-impermeable outer cover; and
    a substantially planar absorbent composite between the body side liner and the outer cover, the absorbent composite having a substantially planar central region selectively stretchable in a longitudinal direction and two substantially planar end regions selectively stretchable in a lateral direction;
    wherein each of the central region and two end regions has an initial length in the longitudinal direction and an initial length in the lateral direction;
    the central region is stretchable to at least 150% of its initial length in the longitudinal direction and only to less than 140% of its initial length in the lateral direction; and
    each of the two end regions is stretchable to at least 150% of its initial length in the lateral direction and only to less than 140% of its initial length in the longitudinal direction.

11. The absorbent article of claim 10, wherein the body side liner comprises a central region selectively stretchable in the longitudinal direction and two end regions selectively stretchable in the lateral direction.

12. The absorbent article of claim 10, wherein the outer cover comprises a central region selectively stretchable in the longitudinal direction and two end regions selectively stretchable in the lateral direction.

13. The absorbent article of claim 10, wherein each of the central and end regions constitutes about 20–60% of a longitudinal length of the absorbent article.

14. The absorbent article of claim 10, wherein each of the central and end regions constitutes about 25–50% of a longitudinal length of the absorbent article.

15. The absorbent article of claim 10, wherein each of the central and end regions constitutes about 30–40% of a longitudinal length of the absorbent article.

16. The absorbent article of claim 10, further comprising:
    a plurality of laterally oriented, stretch-inhibiting bond lines in the central region; and
    a plurality of longitudinally oriented, stretch-inhibiting bond lines in the two end regions.

17. The absorbent article of claim 10, wherein the absorbent composite in each of the central and end regions comprises a neck-bonded laminate of a necked nonwoven fibrous layer and an elastic layer.

18. A diaper comprising the absorbent article of claim 10.

19. Training pants comprising the absorbent article of claim 10.

20. Swim wear comprising the absorbent article of claim 10.

21. Underpants comprising the absorbent article of claim 10.

22. An adult incontinence garment comprising the absorbent article of claim 10.

23. A feminine hygiene product comprising the absorbent article of claim 10.

24. A medical absorbent product comprising the absorbent article of claim 10.

25. An absorbent composite, comprising:
    a central region selectively stretchable in a longitudinal direction and two end regions selectively stretchable in a lateral direction;
    the two end regions attached to the central region along opposite edges of the central region; and the central and end regions comprising a selectively stretchable two substrate laminate having a plurality of pockets formed therein, and a superabsorbent material in the pockets;

wherein each of the central region and two end regions has an initial length in the longitudinal direction and an initial length in the lateral direction;

the central region is stretchable to at least 150% of its initial length in the longitudinal direction and only to less than 140% of its initial length in the lateral direction; and each of the two end regions is stretchable to at least 150% of its initial length in the lateral direction and only to less than 140% of its initial length in the longitudinal direction.

26. A diaper comprising the absorbent composite of claim 25.

27. Training pants comprising the absorbent composite of claim 25.

28. Swim wear comprising the absorbent composite of claim 25.

29. Underpants comprising the absorbent composite of claim 25.

30. An adult incontinence garment comprising the absorbent composite of claim 25.

31. A feminine hygiene product comprising the absorbent composite of claim 25.

32. A medical absorbent product comprising the absorbent composite of claim 25.

* * * * *